United States Patent [19]

Jessel, Jr. et al.

[11] Plant 4,104

[45] Sept. 13, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 703,901

[22] Filed: July 9, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

This invention relates to an induced mutation of Tantalizer chrysanthemum, differing therefrom by its golden yellow florets.

4 Drawing Figures

The present invention comprises a new and distinct cultivar of *Chrysanthemum morifolium,* Ramat., hereinafter referred to by the cultivar name Scintalizer (No. 72097B02).

Scintalizer is a product of a planned sport induction program which had the objective of expanding the color range of the parental cultivar, Tantalizer (No. 72097002; disclosed in U.S. Plant Pat. No. 3,906.) Tantalizer was originated by the present inventors in 1971 as a product of a planned breeding program.

Scintalizer is an induced sport of Tantalizer. Scintalizer was discovered and selected by Walter H. Jessel, Jr. and William E. Duffett on May 1, 1975 as one plant within a flowering block of Tantalizer in a controlled environment in Barberton, Ohio. Plants within the flowering block were derived from stock plants which had been irradiated as rooted cuttings with an x-ray source of 2600 *r* units.

The first act of asexual reproduction of Scintalizer was accomplished when vegetative cuttings were taken from the initial selection in September, 1975 in a controlled environment in Barberton, Ohio by a technician working under formulations established and supervised by Walter H. Jessel, Jr. and William E. Duffett. Horticultural examination of selected units initiated May 1, 1975 has demonstrated that the combination of characteristics as herein disclosed for Scintalizer are firmly fixed and are retained through successive generations of asexual reproduction.

Scintalizer has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in Figure 14.14 in ASHAE Trans., Vol. 64, page 64, and reference is made thereto.

The following traits have been repeatedly observed and are determined to be basic characteristics of Scintalizer which in combination distinguish this chrysanthemum as a new and distinct cultivar:

1. Daisy inflorescence type with moderate longitudinal petal roll in opening stages.
2. Flat inflorescence form which reflexes slightly with age.

3. Diameter across face of inflorescence up to 4.0 inches at maturity.
4. Golden yellow ray floret color with slight bronzy overtones.
5. Medium green disc floret color at immature, unopened stage.
6. Minimal pollen development.
7. Uniform 9 week flowering response.
8. Very tall plant height.
9. Semi-upright branching pattern.
10. High percentage gradeout in top grades (SAF standards).
11. Thin and weak peduncles during high light, high temperature periods (June through September).

The accompanying photographic drawings show typical inflorescence and foliage characteristics of Scintalizer with colors being as nearly true as possible with illustrations of this type. Sheet 1 is a color photograph of Scintalizer. Sheet 2 is a black and white photograph showing three views of the inflorescence of Scintalizer. Sheet 3 is a black and white photograph of the foliage of Scintalizer at three stages of growth.

Of the many commercial cultivars known to the present inventors, the most similar existing cultivar in comparison to Scintalizer is the parental cultivar, Tantalizer. Reference is made to attached Chart B which compares certain characteristics of Tantalizer with the same characteristics of Scintalizer. In comparison to Tantalizer, Scintalizer has different ray floret color. The diameter across face of inflorescence, gradeout (SAF standards), plant height, flowering response period and inflorescence type of Scintalizer are similar to those of Tantalizer.

In the following description, color references are made to The Munsell Limit Color Cascade, 1972 edition. The color values were determined between 3:30 and 4:00 P.M. on Apr. 2, 1976 under 200 foot-candle light intensity at Barberton, Ohio.

Botanical classification: *Chrysanthemum morifolium,* Ramat., cv Scintalizer.

INFLORESCENCE

Capitulum (See Drawing Sheets 1 and 2):

*Form.*—Flat, reflexing slightly with age.

*Type.*—Daisy.

*Permanence.*—10–14 days.

*Diameter across face.*—2.75 to 4.0 inches.

Corolla of ray florets:

*Persistence.*—Resists shatter.

*Color (abaxial).*—27-7 to 27-5.

*Color (adaxial).*—27-4 to 26-4.

Corolla of disc florets:

*Color.*—23-10 (immature) to 27-6 (mature).

Reproductive organs:

*Androecium.*—Numerous; scant pollen.

*Gynoecium.*—Present both ray and disc florets.

PLANT

General appearance: semi-upright; very tall height.

Duration and texture: perennial; herbaceous.

Foliage (See Drawing Sheet 3):

*Color (abaxial).*—Approximately 21-14.

*Color (adaxial).*—Approximately 20-15 overlaid with white.

We claim:

1. A new and distinct cultivar of chrysanthemum known by the cultivar name Scintalizer and characterized particularly as to uniqueness by the combined characteristics of daisy inflorescence type with moderate longitudinal petal roll in opening stages, flat inflorescence from which reflexes slightly with age, diameter across face of inflorescence up to 4.0 inches at maturity, golden yellow ray floret color with slight bronzy overtones, medium green disc floret color at immature, unopened stage, minimal pollen development, uniform nine week flowering response, very tall plant height, semiupright branching habit, high percentage gradeout in top grades (SAF standards), and by its thin and weak peduncles during high light, high temperature periods (June through September).

* * * * *

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off-7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

COMPARISON OF SCINTALIZER AND TANTALIZER

| NAME | RAY FLORET COLOR | DIAMETER ACROSS FACE OF INFLORESCENCE | GRADEOUT | PLANT HEIGHT | RESPONSE PERIOD | INFLORESCENCE TYPE |
|---|---|---|---|---|---|---|
| Scintalizer | Golden yellow | 2.75 inches to 4.0 inches | High | Very tall | 9 weeks | Daisy |
| Tantalizer | Orange bronze | 3.0 inches to 4.0 inches | High | Very tall | 9 weeks | Daisy |

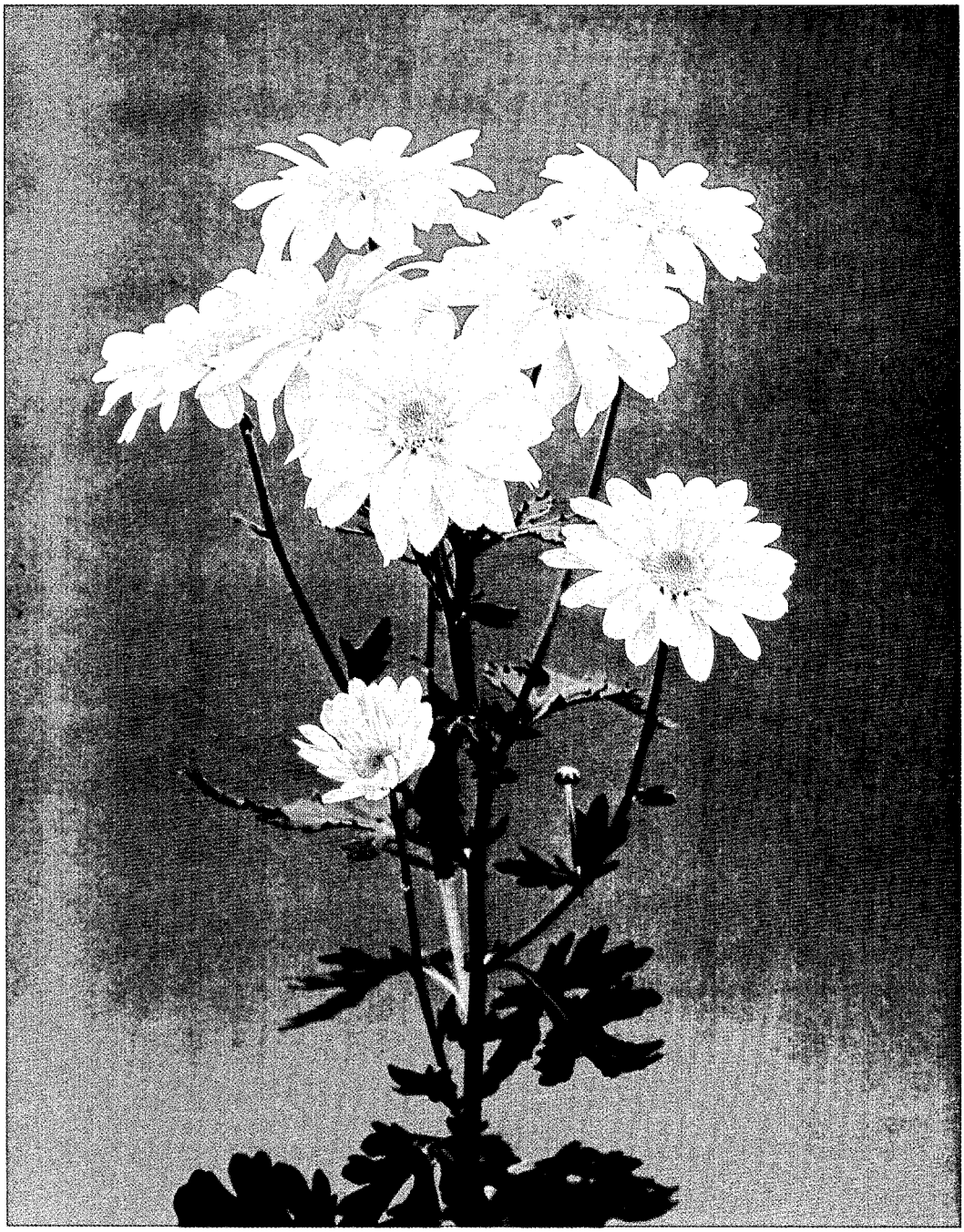

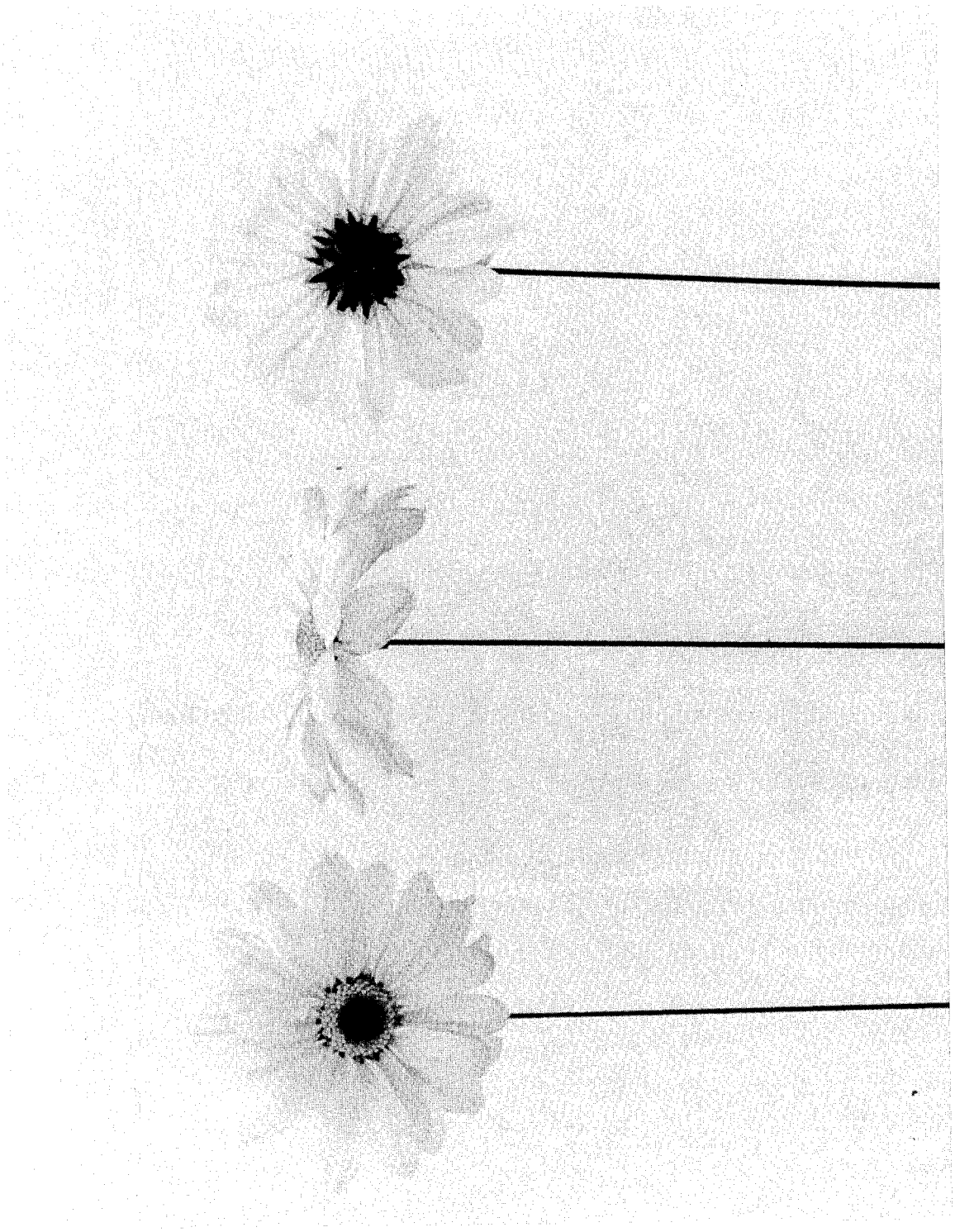

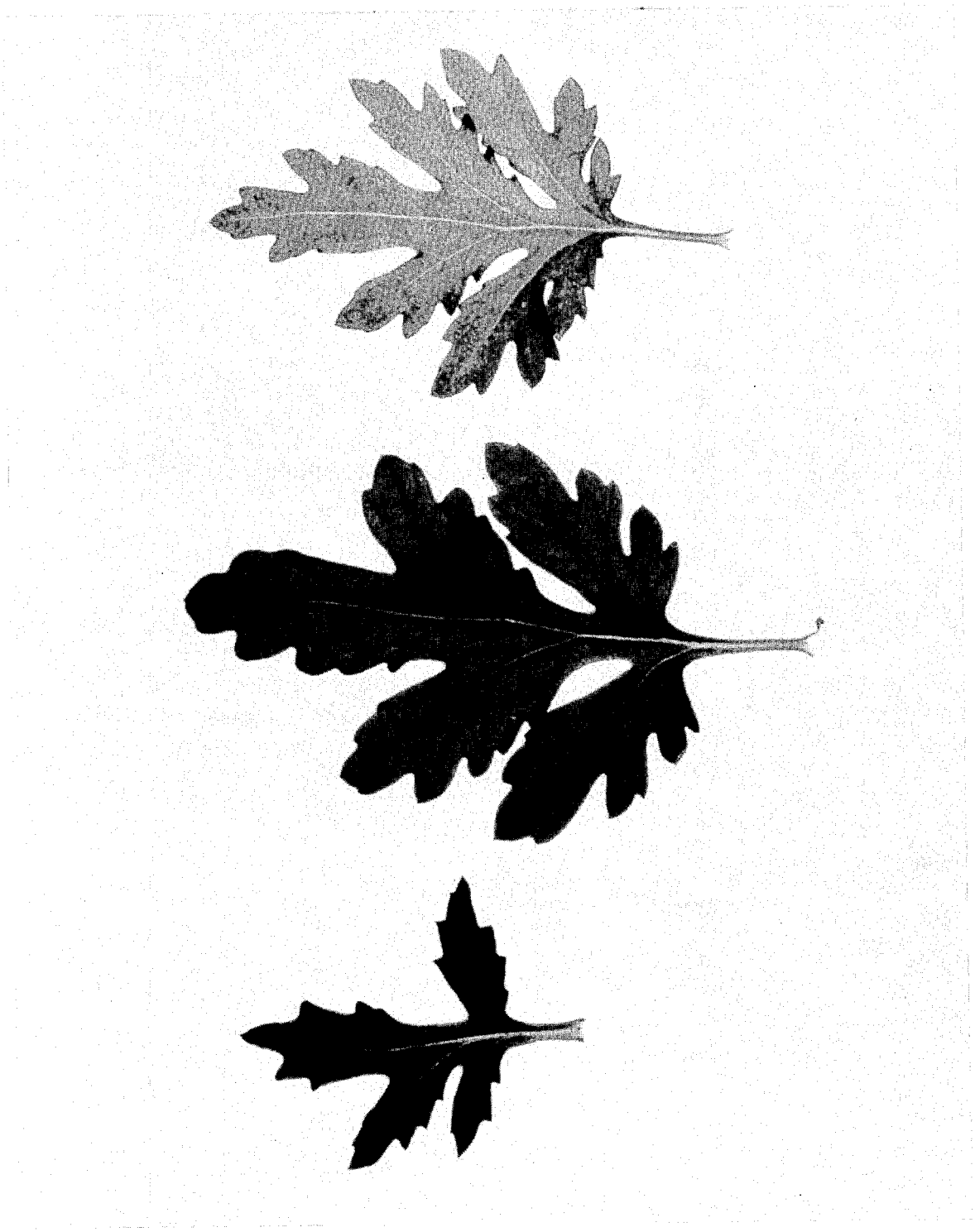

COMPARISONS MADE OF PLANTS GROWN IN A GREENHOUSE IN BARBERTON, OHIO UNDER CONDITIONS AS DESCRIBED IN CHART A.